United States Patent [19]
Urano et al.

[11] Patent Number: 5,220,054
[45] Date of Patent: Jun. 15, 1993

[54] PROCESS FOR PRODUCING AMINOCARBOXYLIC ACID SALT

[75] Inventors: Yoshiaki Urano, Kawasaki; Yukio Kadono; Takakiyo Goto, both of Yokohama, all of Japan

[73] Assignee: Nippon Shokubai Co., Ltd., Osaka, Japan

[21] Appl. No.: 915,803

[22] PCT Filed: Nov. 26, 1991

[86] PCT No.: PCT/JP91/01616
§ 371 Date: Jul. 27, 1992
§ 102(e) Date: Jul. 27, 1992

[87] PCT Pub. No.: WO92/09559
PCT Pub. Date: Jun. 11, 1992

[30] Foreign Application Priority Data

Nov. 27, 1990 [JP] Japan .................... 2-326251
Dec. 28, 1990 [JP] Japan .................... 2-408770
May 17, 1991 [JP] Japan .................... 3-113289

[51] Int. Cl.$^5$ .................. C07C 51/295; C07C 229/08
[52] U.S. Cl. ...................... 562/539; 562/526; 562/538
[58] Field of Search ............ 562/538, 526, 531, 534, 562/539

[56] References Cited

U.S. PATENT DOCUMENTS 3,833,650  9/1974  Schulze et al. ............ 562/526
3,842,081  10/1974  Schulze et al. ............ 562/526
4,782,183  11/1988  Goto et al. ............ 562/539 X

FOREIGN PATENT DOCUMENTS 60-41645   3/1985  Japan.
60-78948   5/1985  Japan.
60-97945   5/1985  Japan.
60-100545  6/1985  Japan.

Primary Examiner—Arthur C. Prescott
Attorney, Agent, or Firm—Sherman & Shalloway

[57] ABSTRACT

The present invention provides a novel process for producing an aminocarboxylic acid salt which is useful as a material for agricultural chemicals and drugs, a chelating agent, a food additive, etc. The process produces an aminocarboxylic acid salt from an aminoalcohol by subjecting the aminoalcohol to an oxidative dehydrogenation reaction in the coexistence of an alkali metal hydroxide and/or an alkaline earth metal hydroxide, a copper-containing catalyst and water, and is characterized by performing the reaction while maintaining the nickel concentration in the reaction mixture at 40 ppm or less.

5 Claims, No Drawings

PROCESS FOR PRODUCING AMINOCARBOXYLIC ACID SALT

TECHNICAL FIELD

The present invention relates to a novel process for producing an aminocarboxylic acid salt which is useful as a material for agricultural chemicals and drugs, a chelating agent, a food additive, etc.

BACKGROUND ART

As the process for industrial production of aminocarboxylic acid salts, there is currently used generally the Strecker process in which a glycine salt, an iminodiacetic acid salt, a nitrilotriacetic acid salt or the like is obtained using hydrocyanic acid and formaldehyde as raw materials. However, since hydrocyanic acid is a virulently poisonous gas, the Strecker process has big limitations in production facility, handling, production site, etc. Moreover, since hydrocyanic acid is mostly obtained as a by-product in acrylonitrile production, the Strecker process has also had a big problem in stable procurement of the raw material.

There are also known processes in which an aminoalcohol is subjected to oxidative dehydrogenation in a caustic alkali to produce an aminocarboxylic acid salt (U.S. Pat. No. 2,384,816, U.S. Pat. No. 2,384,817, U.S. Pat. No. 3,535,373, U.S. Pat. No. 3,842,081, U.S. Pat. No. 3,739,021, etc.). U.S. Pat. No. 2,384,816 discloses a process in which an aminoalcohol and an alkali metal hydroxide are reacted using no catalyst. The process, however, requires a long reaction time and moreover produces an aminocarboxylic acid salt at a low yield. U.S. Pat. No. 2,384,817 discloses a process in which monoethanolamine and potassium hydroxide are reacted in the presence of a copper catalyst and in the absence of water to obtain potassium glycinate. According to the finding by the present inventors, the process produces said glycinate at an insufficient yield. U.S. Pat. No. 3,578,709 discloses a process in which triethanolamine and an alkali hydroxide are reacted in the presence of a zinc oxide catalyst to obtain a nitrilotriacetic acid salt. The process is not satisfactory in the yield of the nitrilotriacetic acid salt. U.S. Pat. No. 3,842,081 discloses the reaction of diethanolamine and potassium hydroxide in the presence of cadmium oxide to obtain potassium iminodiacetate at a relatively high yield. U.S. Pat. No. 3,535,373, U.S. Pat. No. 3,578,709 and U.S. Pat. No. 3,739,021 disclose the reaction of triethanolamine and an alkali hydroxide in the presence of cadmium oxide to obtain a nitrilotriacetic acid salt at a relatively high yield. In these processes using cadmium oxide as a catalyst, however, there is a fear that the reaction products are contaminated with toxic cadmium compounds; accordingly, the products have no utilizability depending upon the applications and moreover there is also a problem of disposing wastes. Therefore, these processes have been unable to become a technique competitive with the Strecker process.

Also, there are known processes in which an aminoalcohol is reacted in the coexistence of an alkali hydroxide, water and a copper-containing catalyst or a copper-zirconium-containing catalyst to obtain an aminocarboxylic acid salt (U.S. Pat. No. 4,782,183). In these processes, however, although the selectivity of desired aminocarboxylic acid salt is high (95 %), the repeated use of catalyst tends to result in a reduced selectivity and increased amounts of by-products. The main by-products are an oxalic acid salt when a glycine salt is produced from monoethanolamine as a raw material, a glycine salt when an iminodiacetic acid salt is produced from diethanolamine as a raw material, and an iminodiacetic acid salt, a glycine salt, etc. when a nitrilotriacetic acid salt is produced from triethanolamine as a raw material. Since these by-products have reactivities similar to those of desired aminocarboxylic acid salt, when the aminocarboxylic acid salt is used as a raw material for agricultural chemicals, drugs, etc., the yield of final product is affected greatly. Therefore, in order to obtain an aminocarboxylic acid salt of high purity, it is necessary to change the catalyst used, in a short period to maintain a high selectivity or to subject the obtained aminocarboxylic acid salt to a complex purification step.

The object of the present invention is to provide a novel process for producing an aminocarboxylic acid salt, which has no toxicity problem, which generates only small amounts of by-products, which gives a high yield and a high selectivity, and accordingly which can produce an aminocarboxylic acid salt economically and advantageously.

DISCLOSURE OF THE INVENTION

In view of the above-mentioned problems, the present inventors made various investigations on the process for producing an aminocarboxylic acid salt from an aminoalcohol by subjecting the aminoalcohol to oxidative dehydrogenation in the presence of a copper-containing catalyst. As a result, the present inventors found that the presence of nickel in reaction mixture increased the amount of the above-mentioned by-products formed. A further investigation has led to the completion of the present invention. According to the present invention, there is provided a process for producing an aminocarboxylic acid salt from an aminoalcohol represented by the general formula (1)

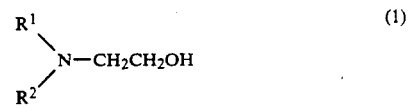

(R$^1$ and R$^2$ are independently a hydrogen atom, a hydroxyethyl group, an alkyl group of 1–18 carbon atoms or an aminoalkyl group of 2–3 carbon atoms) by subjecting the aminoalcohol to an oxidative dehydrogenation reaction in the coexistence of an alkali metal hydroxide and/or an alkaline earth metal hydroxide, a copper-containing catalyst and water, which process is characterized by performing the reaction while maintaining the nickel concentration in reaction mixture at 40 ppm or less.

By the process of the present invention, the CH$_2$OH group of the aminoalcohol represented by the general formula (1) is oxidatively dehydrogenated to become a COOH group. When the R$^1$ and R$^2$ of the general formula (1) are each a hydroxyethyl group, these CH$_2$OH groups are also oxidatively dehydrogenated to each become a COOH group. Therefore, it is also included in the present invention to obtain an aminocarboxylic acid salt having a plurality of COOH groups.

The aminoalcohol represented by the general formula (1) includes, for example, monoethanolamine, diethanolamine, triethanolamine, N-methylethanolamine, N-ethylethanolamine, N-isopropylethanolamine, N-butylethanolamine, N-nonylethanolamine, N-(2- aminoethyl)ethanolamine, N-(3-aminopropyl)ethanolamine, N,N-dimethylethanolamine, N,N-diethylethanolamine, N,N-dibutylethanolamine, N-methyldiethanolamine, N-ethyldiethanolamine, N-isopropyldiethanolamine, N-butyldiethanolamine, N-ethyl-N-(2-aminoethyl)ethanolamine, N-methyl-N-(3-aminopropyl)ethanolamine, etc.

Using these aminoalcohols as raw materials, corresponding aminocarboxylic acid salts can be produced. As specific examples of the aminocarboxylic acids, there can be mentioned glycine, iminodiacetic acid, nitrilotriacetic acid, N-methylglycine, N-ethylglycine, N-isopropylglycine, N-butylglycine, N-nonylglycine, N-(2-aminoethyl)glycine, N-(3-aminopropyl)glycine, N,N-copper formate, copper carbonate or the like to thermal decomposition and/or reduction, as they are or by allowing them to be supported on an alkali-resistant carrier. The use of these catalysts by allowing them to be supported on an alkali-resistant carrier, has an advantage in that the catalysts can be easily separated from the reaction mixture after the intended reaction and accordingly can be easily reclaimed for reuse. Viewed from the activity and life of catalyst, particularly preferable catalysts are a developed Raney copper and a catalyst obtained by allowing copper to be supported on zirconium oxide or silicon carbide by a coprecipitation method or an impregnation method.

The catalyst used in the present invention, preferably has a low nickel content. When the nickel content is high, the nickel in the catalyst dissolves in the reaction mixture, which becomes a major cause for the nickel concentration in the reaction mixture to increase. When, for example, developed Raney copper is used, developed Raney copper available on the market contains about several thousand ppm of nickel ordinarily. The catalyst used in the practice of the present invention, contains nickel at a concentration of preferably 0.3 % by weight or less, more preferably 0.1 % by weight or less.

Further, a catalyst having too small a particle size is disadvantageous in catalyst separation. For example, when the catalyst separation is effected by precipitation, the precipitation rate is low; when the catalyst separation is effected by filtration, the filtration rate is low. Meanwhile, with a catalyst having too large a particle size, its precipitation is better, but a larger agitation power is required in order to obtain good catalyst dispersion and the small effective surface area of the catalyst makes the catalyst activity low. Consequently, the particle size of the catalyst is preferably in the range of 2–300μ. However, dimethylglycine, N,N-diethylglycine, N,N-dibutylglycine, N-methyliminodiacetic acid, N-ethyliminodiacetic acid, N-isopropyliminodiacetic acid, N-butyliminodiacetic acid, N-ethyl-N-(2-aminoethyl)glycine, N-methyl-N-(3-aminopropyl)glycine, etc. In the process of the present invention, each of these aminocarboxylic acids is produced in the form of an alkali metal salt and/or an alkaline earth metal salt.

In the present invention, the reaction is conducted while the nickel concentration in reaction mixture is being maintained at 40 ppm or less, preferably 30 ppm or less. Nickel is present in the reaction mixture in the form of ion or colloidal metal and affects the capability of the catalyst used. If the reaction is conducted under the conditions not satisfying the above requirement, the amount of the by-products formed becomes larger. The major causes for nickel to come into the reaction mixture are presumed to be that nickel is contained in the aminoalcohol (raw material), alkali metal hydroxide, alkaline earth metal hydroxide, water or catalyst used, or the nickel as a constituent material of reactor, apparatuses attached thereto, pipes, etc. dissolves in or comes into the reaction mixture.

The catalyst used in the present invention contains copper as an essential component. As the copper source, there can be used metallic copper; copper oxides; copper hydroxide; inorganic copper salts, for example, copper nitrate, sulfate, carbonate, halides, etc.; and organic copper salts, for example, copper formate, acetate, propionate, lactate, etc. The form of the catalyst is not particularly restricted. There can be used, for example, a catalyst obtained by oxidizing the surface of metallic copper and then reducing the resulting surface with hydrogen, a catalyst obtained by developing a Raney copper with an aqueous alkali solution, and an activated copper obtained by subjecting when the reaction is conducted using a fixed-bed flow reactor, a catalyst of larger particle size is suitable because the pressure loss must be made small.

Further, the catalyst used in the present invention, preferably has a specific surface area of 1 $m^2/g$ or more as measured by the BET method because too small a specific surface area results in low catalyst activity and a large amount of a catalyst must be used.

The alkali metal hydroxide or the alkaline earth metal hydroxide, used in the present invention is particularly preferably sodium hydroxide, potassium hydroxide, etc. These can be sued in the form of flakes, a powder, pellets, an aqueous solution or the like. The use in the form of an aqueous solution is preferable in view of handleability. The amount of alkali metal hydroxide or alkaline earth metal hydroxide used is at least one equivalent, preferably 1.0–2.0 equivalents to the hydroxyl group of the aminoalcohol used in the reaction.

The process of the present invention is performed in the presence of water. The use of water has a merit in that an aminoalcohol and an alkali metal hydroxide and/or an alkaline earth metal hydroxide can be reacted in a uniform system, and is essential in order to obtain an aminocarboxylic acid salt at a high yield. The amount of water used in the reaction is 10 % by weight or more, preferably 50–500 % by weight based on the aminoalcohol.

The reaction temperature is ordinarily 220° C. or lower, preferably 120°–210° C., particularly preferably 140°–200° C. in order to prevent the thermal decomposition and hydrogenolysis of the carbon-nitrogen bonds of the aminoalcohol and the formed aminocarboxylic acid.

The reaction pressure is preferably as low as possible in view of the reaction rate. There is used ordinarily at least a lowest pressure required to allow the reaction to proceed in a liquid phase, preferably a pressure of 5–50 $kg/cm^2G$.

The material of the reactor in which the oxidative dehydrogenation of the present invention is conducted, must be withstand severe reaction conditions (strong basicity, high temperature, high pressure, generation of hydrogen). In this respect, nickel, a nickel alloy, titanium, etc. are suitable. Copper can also be used, but operational control must be made thoroughly in order to prevent the contamination with oxygen because the contamination invites corrosion.

When the material of the reactor is nickel or a nickel alloy, in particular, the reactor wall is worn by the collision of the catalyst suspended in the reaction mixture, which becomes a major cause for incoming of nickel into the reaction mixture. Therefore, it is necessary to thoroughly investigate the reaction conditions such as agitation power, catalyst concentration, reaction time and the like in order to ensure that the nickel concentration in the reaction mixture is not higher than 40 ppm. With respect to the agitation power, in particular, too strong an agitation power makes severe the wear of the reactor wall by the catalyst suspended in the reaction mixture; too weak an agitation power invites the precipitation of the catalyst making low the reaction rate. Therefore, it is preferable to conduct the reaction using an agitation power of 0.01-1.5 kw per $m^3$ of reaction mixture. Too large a catalyst amount promotes the wear of the reactor wall as well. Therefore, it is preferable to conduct the reaction using the catalyst in an amount of preferably 1-70 % by weight, preferably 5-50 % by weight based on the aminoalcohol. Further, when the catalyst is recovered and reused, the nickel in the reaction mixture is partially absorbed by the catalyst and the adsorbed nickel dissolves in the reaction mixture in a new reaction; therefore, the higher frequency of repeated use of catalyst tends to give a larger amount of by-products.

The type of the reaction may be any of a batch reaction, a semibatch reaction and a continuous reaction.

The catalyst is removed, by filtration, from the reaction mixture after the reaction, whereby an aqueous solution of an intended aminocarboxylic acid salt is obtained as a filtrate. It is appropriately purified as necessary, whereby a high quality aminocarboxylic acid salt can be obtained as a product. Meanwhile, the catalyst removed by filtration is recovered and can be reused in a new reaction as it is. Needless to say, the recovered catalyst may be appropriately reclaimed as necessary and reused.

EFFECTS OF THE INVENTION

According to the process of the present invention, the amount of by-products formed is small; an intended aminocarboxylc acid salt can be produced at a high yield and at a high selectivity; and a product of high quality can be supplied at a low cost.

BEST MODE FOR CARRYING OUT THE INVENTION

The present invention is hereinafter described specifically by way of Examples. However, the present invention is by no means restricted by these Examples.

Herein, the conversion of aminoalcohol and the selectivity of aminocarboxylic acid are derived from the following formulas.

---

Conversion of aminoalcohol (%) =
(moles of aminoalcohol reacted) ÷ (moles of aminoalcohol fed for reaction) × 100
Selectivity of aminocarboxylic acid (%) =
(mole of aminocarboxylic acid formed) ÷ (moles of aminoalcohol reacted) × 100

---

EXAMPLE 1a 80 g of diethanolamine, 64 g of sodium hydroxide, 170 g of water and 8 g of developed Raney copper having an average particle diameter of 20μ and a BET surface area of 19 $m^2/g$ (this copper contained 0.03 % by weight of nickel as an impurity) were fed into a nickel-made autoclave having an internal volume of 500 ml, provided with a siphon with a filter. The number of rotations was controlled (500 rpm) so that the agitation power of agitator became 0.3 kg/$m^3$ of reaction mixture. The inside of the autoclave was purged with hydrogen gas three times. Then, a reaction was conducted at a reaction temperature of 170° C. at a reaction pressure of 10 kg/$cm^2$G until there was no generation of hydrogen. The time required for the reaction was 5 hours after the temperature of the reaction system had been elevated to 170° C.

After the completion of the reaction, the reaction mixture was allowed to stand to precipitate the catalyst, and the reaction mixture was taken out from the siphon. The reaction mixture was analyzed. It indicated that the conversion of diethanolamine was 99.5 %, the selectivity of disodium iminodiacetate was 98.5 % and the selectivity of sodium glycinate as a by-product was 1.1 %. The reaction mixture taken out showed no presence of suspended matter, and analysis by atomic absorption spectrometry indicated that the nickel concentration in the reaction mixture was 1.7 ppm.

EXAMPLE 1b

In order to examine the catalyst capability in repeated use, repeat tests were conducted under the same reaction conditions as in Example 1a, using the catalyst which had remained in the autoclave after Example 1a.

In the 10th repeat test, the time required for reaction was 10 hours after the temperature elevation, and the analysis of the reaction mixture indicated that the conversion of diethanolamine was 99.6 %, the selectivity of disodium iminodiacetate was 96.7 % and the selectivity of sodium glycinate as a by-product was 2.6%. Analysis by atomic absorption spectrometry indicated that the nickel concentration in the reaction mixture was 20 ppm.

EXAMPLE 2

A reaction was conducted in the same manner as in Example 1a except that the amount of catalyst used was 16 g.

The reaction conditions and the results were shown in Table 1.

EXAMPLE 3

A reaction was conducted in the same manner as in Example 1a except that the amount of catalyst used was 16 g and the agitation power employed was 1.2 kw/$m^3$ (850 rpm).

The reaction conditions and the results were shown in Table 1.

EXAMPLE 4

A reaction was conducted in the same manner as in Example 1a except that the amount of catalyst used was 24 g.

The reaction conditions and the results were shown in Table 1.

EXAMPLE 5

A reaction was conducted in the same manner as in Example 1a except that the amount of catalyst used was 40 g.

The reaction conditions and the results were shown in Table 1.

EXAMPLE 6

A reaction was conducted in the same manner as in Example 1a except that the amount of catalyst used was 40 g and the agitation power employed was 1.8 kg/m$^3$ (1000 rpm).

The reaction conditions and the results were shown in Table 1.

EXAMPLE 7a

A reaction was conducted in the same manner as in Example 1a except that the amount of catalyst used was 16 g and the reaction temperature used was 160° C.

The reaction conditions and the results were shown in Table 1.

EXAMPLE 7b

Repeat tests were conducted under the same reaction conditions as in Example 7a, using the catalyst which had remained in the autoclave after Example 7a.

The reaction conditions and results of the 10th repeat test were shown in Table 1.

EXAMPLE 8

A reaction was conducted in the same manner as in Example 1a except that the amount of catalyst used was 16 g, the reaction temperature used was 160° C. and the agitation power used was 1.2 kw/m$^3$ (850 rpm).

The reaction conditions and the results were shown in Table 1.

EXAMPLE 9

A reaction was conducted in the same manner as in Example 1a except that there was used 16 g of developed Raney copper containing 0.2% by weight of nickel as an impurity.

The reaction conditions and the results were shown in Table 1.

EXAMPLE 10

A reaction was conducted in the same manner as in Example 1a except that there was used 16 g of developed Raney copper containing 0.3 % by weight of nickel as an impurity.

The reaction conditions and the results were shown in Table 1.

EXAMPLE 11

A reaction was conducted in the same manner as in Example 1a except that there was used 16 g of developed Raney copper containing 0.5 % by weight of nickel as an impurity.

The reaction conditions and the results were shown in Table 1.

EXAMPLE 12a

An aqueous sodium hydroxide solution was added to a solution of 24.8 g of zirconium oxychloride and 4.0 g of copper nitrate dissolved in 300 ml of water, to precipitate hydroxides. The precipitate was washed with water, dried, subjected to a heat treatment in air at 500° C. for 3 hours, and subjected to a reduction treatment in a hydrogen stream at 230° C. for 6 hours to prepare a copper- and zirconium-containing catalyst. The catalyst had an average particle diameter of 2$\mu$ and a BET surface area of 61 m$^2$/g. Analysis by atomic absorption spectrometry detected no nickel (less than 0.01 % by weight).

A reaction was conducted under the same conditions as in Example 1a except that 8 g of the above copper- and zirconium-containing catalyst was used in place of the developed Raney copper.

The reaction conditions and the results were shown in Table 1.

EXAMPLE 12b

Repeat tests were conducted under the same reaction conditions as in Example 12a, using the catalyst which had remained in the autoclave after Example 12a.

The reaction conditions and results of the 10th repeat test were shown in Table 1.

EXAMPLE 13a

A reaction was conducted in the same manner as in Example 1a except that a titanium-made autoclave was used in place of the nickel-made autoclave.

The reaction conditions and results of the 10th repeat test were shown in Table 1.

EXAMPLE 13b

Repeat tests were conducted under the same reaction conditions as in Example 13a, using the catalyst which had remained in the autoclave after Example 13a.

The reaction conditions and results of the 10th repeat test were shown in Table 1.

EXAMPLE 14a

A reaction was conducted in the same manner as in Example 1a except that an autoclave made of stainless steel having a copper lining was used in place of the nickel-made autoclave.

The reaction conditions and the results were shown in Table 1.

EXAMPLE 14b

Repeat tests were conducted under the same reaction conditions as in Example 14a, using the catalyst which had remained in the autoclave after Example 14a.

The reaction conditions and results of the 10th repeat test were shown in Table 1.

EXAMPLE 15a

A reaction was conducted in the same manner as in Example 12a except that an autoclave made of stainless steel having a copper lining was used in place of the nickel-made autoclave.

The reaction conditions and the results were shown in Table 1.

EXAMPLE 15b

Repeat tests were conducted under the same reaction conditions as in Example 15a, using the catalyst which had remained in the autoclave after Example 15a.

The reaction conditions and results of the 10th repeat test were shown in Table 1.

EXAMPLE 16

171 g of monoethanolamine, 123 g of sodium hydroxide, 262 g of water and 34 g of developed Raney copper having an average particle diameter of 20$\mu$ and a BET surface area of 19 m$^2$/g (this copper containing 0.03% by weight of nickel as an impurity) were fed into a nickel-made autoclave having an internal volume of 1000 ml. The number of rotations was controlled (500 rpm) so that the agitation power of agitator became 0.3 kw per m$^3$ of reaction mixture. The inside of the autoclave was purged with hydrogen gas three times. Then, a reaction was conducted at a reaction temperature of 160° C. at a reaction pressure of 10 kg/cm²G until there was no generation of hydrogen. The time required for the reaction was 4 hours after the temperature of the reaction system had been elevated to 160° C.

After the completion of the reaction, the reaction mixture was taken out and analyzed, in the same manner as in Example 1a. As a result, the conversion of monoethanolamine was 99.5%, the selectivity of sodium glycinate was 99.8%, and the selectivity of disodium oxalate formed as a by-product was 0.2%.

The reaction conditions and the results were shown in Table 2.

EXAMPLE 17

118 g of triethanolamine, 146 g of potassium hydroxide, 333 g of water and 35 g of developed Raney copper having an average particle diameter of 20μ and a BET surface area of 19 m²/g (this copper contained 0.03% by weight of nickel as an impurity) were fed into a nickel-made autoclave having an internal volume of 1000 ml. The number of rotations was controlled (500 rpm) so that the agitation power of agitator became 0.3 kw per m³ of reaction mixture. The inside of the autoclave was purged with hydrogen gas three times. Then, a reaction was conducted at a reaction temperature of 190° C. at a reaction pressure of 10 kg/cm²G until there was no generation of hydrogen. The time required for the reaction was 10 hours after the temperature of the reaction system had been elevated to 190° C.

After the completion of the reaction, the reaction mixture was taken out and analyzed, in the same manner as in Example 1a. As a result, the conversion of olamine was 98.0%, the selectivity of trisodium nitrilotriacetate was 95.1%, and the selectivity of iminodiacetate formed as a by-product was 4.1%.

The reaction conditions and the results were shown in Table 2.

TABLE 1

| | Feeding into reactor | | | | | Reaction conditions | | | | |
|---|---|---|---|---|---|---|---|---|---|---|
| | Diethanol- | NaOH | Water | | | Material | Temp. | Time | Agitation conditions | |
| Example | amine g | g | g | Catalyst (Ni wt. %) | g | of reactor | °C. | hr | rpm | kw/m³ |
| 1a | 80 | 64 | 170 | Developed Raney copper (0.03) | 8 | Ni | 170 | 5 | 500 | 0.3 |
| 1b | | | | Ditto (after 10 times of recycling) (0.05) | 8 | | | 10 | | |
| 2 | 80 | 64 | 170 | Developed Raney copper (0.03) | 16 | Ni | 170 | 4 | 500 | 0.3 |
| 3 | 80 | 64 | 170 | Developed Raney copper (0.03) | 16 | Ni | 170 | 4 | 850 | 1.2 |
| 4 | 80 | 64 | 170 | Developed Raney copper (0.03) | 24 | Ni | 170 | 4 | 500 | 0.3 |
| 5 | 80 | 64 | 170 | Developed Raney copper (0.03) | 40 | Ni | 170 | 4 | 500 | 0.3 |
| 6 | 80 | 64 | 170 | Developed Raney copper (0.03) | 40 | Ni | 170 | 4 | 1000 | 1.8 |
| 7a | 80 | 64 | 170 | Developed Raney copper (0.03) | 16 | Ni | 160 | 5 | 500 | 0.3 |
| 7b | | | | Ditto (after 10 times of recycling) (0.05) | 16 | | | 10 | | |
| 8 | 80 | 64 | 170 | Developed Raney copper (0.03) | 16 | Ni | 160 | 5 | 850 | 1.2 |
| 9 | 80 | 64 | 170 | Developed Raney copper (0.2) | 16 | Ni | 170 | 4 | 500 | 0.3 |
| 10 | 80 | 64 | 170 | Developed Raney copper (0.3) | 16 | Ni | 170 | 4 | 500 | 0.3 |
| 11 | 80 | 64 | 170 | Developed Raney copper (0.5) | 16 | Ni | 170 | 4 | 500 | 0.3 |
| 12a | 80 | 64 | 170 | Cu/Zr (<0.01) | 8 | Ni | 170 | 5 | 500 | 0.3 |
| 12b | | | | Ditto (after 10 times of recycling) (0.05) | 8 | | | 10 | | |
| 13a | 80 | 64 | 170 | Developed Raney copper (0.03) | 8 | Ti | 170 | 5 | 500 | 0.3 |
| 13b | | | | Ditto (after 10 times of recycling) (0.03) | 8 | | | 13 | | |
| 14a | 80 | 64 | 170 | Developed Raney copper (0.03) | 8 | Cu-clad SUS | 170 | 5 | 500 | 0.3 |
| 14b | | | | Ditto (after 10 times of recycling) (0.03) | 8 | | | 10 | | |
| 15a | 80 | 64 | 170 | Cu/Zr (<0.01) | 8 | Cu-clad SUS | 170 | 5 | 500 | 0.3 |
| 15b | | | | Ditto (after 10 times of recycling) (<0.01) | 8 | | | 10 | | |

| Example | Ni conc. in reaction mixture ppm | Diethanol-amine conversion mol % | Iminodi-acetic acid selectivity mol % | Glycine selectivity mol % |
|---|---|---|---|---|
| 1a | 1.7 | 99.5 | 98.5 | 1.1 |
| 1b | 20 | 99.6 | 96.7 | 2.6 |
| 2 | 2.7 | 99.6 | 97.7 | 1.5 |
| 3 | 3.3 | 99.5 | 98.2 | 1.4 |
| 4 | 10 | 99.8 | 97.6 | 2.0 |
| 5 | 22 | 99.9 | 96.7 | 2.6 |
| 6 | 36 | 99.5 | 95.1 | 4.4 |
| 7a | 1.2 | 99.6 | 99.1 | 0.8 |
| 7b | 18 | 99.4 | 97.5 | 2.4 |
| 8 | 2.2 | 99.3 | 98.7 | 1.0 |
| 9 | 6.1 | 99.6 | 98.3 | 1.6 |
| 10 | 9.3 | 99.5 | 98.1 | 1.6 |
| 11 | 32 | 99.4 | 95.6 | 4.0 |
| 12a | 7.5 | 99.3 | 98.0 | 1.6 |
| 12b | 28 | 97.5 | 96.5 | 2.8 |
| 13a | <1 | 98.5 | 99.1 | 0.5 |
| 13b | <1 | 98.5 | 98.7 | 1.0 |
| 14a | <1 | 99.0 | 99.3 | 0.5 |
| 14b | <1 | 99.0 | 98.4 | 1.2 |
| 15a | <1 | 99.0 | 99.5 | 0.4 |

TABLE 1-continued

| | | | | | | | 15b | <1 | 98.5 | 99.0 | 0.8 |

TABLE 2

| | Feeding into reactor | | | | Reaction conditions | | | | |
| --- | --- | --- | --- | --- | --- | --- | --- | --- | --- |
| | Amino- | Hydroxide | Water | | | Material | Temp. | Time | Agitation conditions |
| Example | alcohol g | g | g | Catalyst (Ni wt. %) | g | of reactor | °C. | hr | rpm | kw/m³ |
| 16 | Monoe-tha-nolamine 171 | NaOH 123 | 262 | Developed Raney copper (0.03) | 34 | Ni | 160 | 4 | 500 | 0.3 |
| 17 | Trietha-nolamine 118 | KOH 146 | 333 | Developed Raney copper (0.03) | 35 | Ni | 190 | 10 | 500 | 0.3 |

| Example | Ni conc. in reaction mixture ppm | Alkanol-amine conversion mol % | Amino-carboxylic acid selectivity mol % | By-product selectivity mol % |
| --- | --- | --- | --- | --- |
| 16 | 1.6 | 99.5 | Glycine 99.8 | Oxalic acid 0.2 |
| 17 | 1.6 | 98.0 | Nitrilotri-acetic acid 95.1 | Iminodi-acetic acid 4.1 |

We claim:

1. A process for producing an aminocarboxylic acid salt from an aminoalcohol represented by the general formula (1)

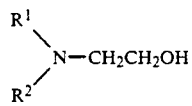

(1)

($R^1$ and $R^2$ are independently a hydrogen atom, a hydroxyethyl group, an alkyl group of 1-18 carbon atoms or an aminoalkyl group of 2-3 carbon atoms) by subjecting the aminoalcohol to an oxidative dehydrogenation reaction in the coexistence of an alkali metal hydroxide and/or an alkaline earth metal hydroxide, a copper-containing catalyst and water, which process is characterized by conducting the reaction while maintaining the nickel concentration in the reaction mixture at 40 ppm or less.

2. The process of claim 1, wherein the reaction is conducted using a copper-containing catalyst containing nickel at a concentration of 0.3% by weight or less.

3. The process of claim 1, wherein the reaction is conducted using the copper-containing catalyst in an amount of 5-50% by weight based on the aminoalcohol represented by the general formula (1).

4. The process of claim 1, wherein the reaction is conducted using an agitation power in the range of 0.1-1.5 kw per m³ of reaction mixture.

5. The process of claim 1, which uses a reactor whose inner wall material contains no nickel.

* * * * *

UNITED STATES PATENT AND TRADEMARK OFFICE
CERTIFICATE OF CORRECTION

PATENT NO. : 5,220,054

DATED : June 15, 1993

INVENTOR(S) : YOSHIAKI URANO, et al.

It is certified that error appears in the above-identified patent and that said Letters Patent is hereby corrected as shown below:

Column 3, lines 15-50, delete in entirety.

line 51, delete "2-300µ. However dimethylglycine" and insert therefore, --N,N-dimethylglycine--.

Column 4, line 18, after "subjecting" insert the following:

--copper formate, copper carbonate or the like to thermal decomposition and/or reduction, as they are or by allowing them to be supported on an alkali-resistant carrier. The use of these catalysts by allowing them to be supported on an alkali-resistant carrier, has an advantage in that the catalysts can be easily separated from the reaction mixture after the intended reaction and accordingly can be easily reclaimed for reuse. Viewed from the activity and life of catalyst, particularly preferable catalysts are a developed Raney copper and a catalyst obtained by allowing copper to be supported on zirconium oxide or silicon carbide by a coprecipitation method or an impregnation method.

The catalyst used in the present invention, preferably has a low nickel content. When the nickel content is high, the nickel in the catalyst dissolves in the reaction mixture, which becomes a major cause for the nickel concentration in the reaction mixture to increase. When, for example, developed Raney copper is used, developed Raney copper available on the market contains about several thousand ppm of nickel ordinarily. The catalyst used in the practice

UNITED STATES PATENT AND TRADEMARK OFFICE
CERTIFICATE OF CORRECTION

PATENT NO. : 5,220,054
DATED : June 15, 1993
INVENTOR(S) : YOSHIAKI URANO, et al.

It is certified that error appears in the above-identified patent and that said Letters Patent is hereby corrected as shown below:

of the present invention, contains nickel at a concentration of preferably 0.3% by weight or less, more preferably 0.1% by weight or less.

Further, a catalyst having too small a particle size is disadvantageous in catalyst separation. For example, when the catalyst separation is effected by precipitation, the precipitation rate is low; when the catalyst separation is effected by filtration, the filtration rate is low. Meanwhile, with a catalyst having too large a particle size, its precipitation is better, but a larger agitation power is required in order to obtain good catalyst dispersion and the small effective surface area of the catalyst makes the catalyst activity low. Consequently, the particle size of the catalyst is preferably in the range of 2-300$\mu$. However,--

Signed and Sealed this

Fifth Day of July, 1994

Attest:

*Attesting Officer*

BRUCE LEHMAN

*Commissioner of Patents and Trademarks*